(12) United States Patent
Nebolon et al.

(10) Patent No.: US 9,039,747 B2
(45) Date of Patent: May 26, 2015

(54) THERMAL THERAPY DEVICE

(71) Applicants: Joseph Francis Nebolon, Del Mar, CA (US); Sarah Joan Gardner, Cardiff, CA (US)

(72) Inventors: Joseph Francis Nebolon, Del Mar, CA (US); Sarah Joan Gardner, Cardiff, CA (US)

(*) Notice: Subject to any disclaimer, the term of this patent is extended or adjusted under 35 U.S.C. 154(b) by 186 days.

(21) Appl. No.: 13/667,877

(22) Filed: Nov. 2, 2012

(65) Prior Publication Data

US 2014/0128947 A1    May 8, 2014

(51) Int. Cl.
A61F 7/10    (2006.01)
A61F 7/02    (2006.01)

(52) U.S. Cl.
CPC ............ *A61F 7/10* (2013.01); *A61F 2007/0209* (2013.01); *A61F 2007/0203* (2013.01); *A61F 2007/0211* (2013.01); *A61F 7/02* (2013.01); *A61F 2007/0214* (2013.01); *A61F 2007/0215* (2013.01)

(58) Field of Classification Search
CPC .............. A61F 2007/0211; A61F 2007/0209; A61F 2007/0214; A61F 7/02; A61F 2007/0215; A61F 2007/209
USPC .................................................. 607/96–114
See application file for complete search history.

(56) References Cited

U.S. PATENT DOCUMENTS

| | | | | |
|---|---|---|---|---|
| 2,366,989 A | * | 1/1945 | Robertson | 62/530 |
| 2,378,087 A | * | 6/1945 | Kearney | 62/530 |
| 3,075,529 A | * | 1/1963 | Young, Jr. | 607/114 |
| 4,462,224 A | * | 7/1984 | Dunshee et al. | 62/530 |
| 4,530,220 A | * | 7/1985 | Nambu et al. | 62/530 |
| 5,031,418 A | * | 7/1991 | Hirayama et al. | 62/530 |
| 5,314,005 A | * | 5/1994 | Dobry | 165/10 |
| 5,476,489 A | * | 12/1995 | Koewler | 607/104 |
| 5,800,491 A | * | 9/1998 | Kolen et al. | 607/108 |
| 6,117,164 A | * | 9/2000 | Gildersleeve et al. | 607/108 |
| 2004/0010302 A1 | * | 1/2004 | von Hoffmann et al. | 607/114 |
| 2004/0244413 A1 | * | 12/2004 | Trinh et al. | 62/530 |
| 2007/0021810 A1 | * | 1/2007 | Paulin | 607/114 |
| 2008/0119916 A1 | * | 5/2008 | Choucair et al. | 607/104 |
| 2009/0076575 A1 | * | 3/2009 | Noel | 607/113 |
| 2010/0010597 A1 | * | 1/2010 | Evans | 607/108 |
| 2012/0316626 A1 | * | 12/2012 | Dolivier et al. | 607/108 |
| 2014/0058326 A1 | * | 2/2014 | Cull | 604/113 |

* cited by examiner

*Primary Examiner* — Linda Dvorak
*Assistant Examiner* — Yasamin Ekrami
(74) *Attorney, Agent, or Firm* — ARC IP Law, PC; Joseph J. Mayo

(57) ABSTRACT

A thermal therapy device comprising a flexible, water-impermeable container containing a plurality of discrete, non-water-soluble hydrophillic absorbers, a hydrating liquid mixture comprising water, means for physically separating at least two adjacent absorbers thereby providing a means for preventing clumping, and a plurality of insulating members. The means for preventing clumping maintaining the pliability of the device in a frozen state after prolonged and extend cycles of freezing/thawing. A rigid storage container is also provided.

14 Claims, 2 Drawing Sheets

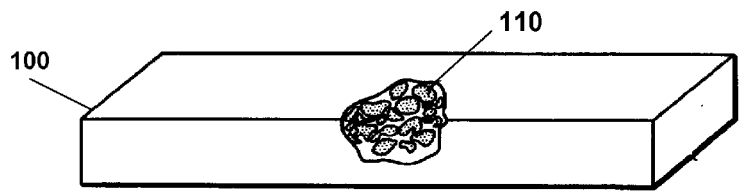
FIG. 1
(PRIOR ART)
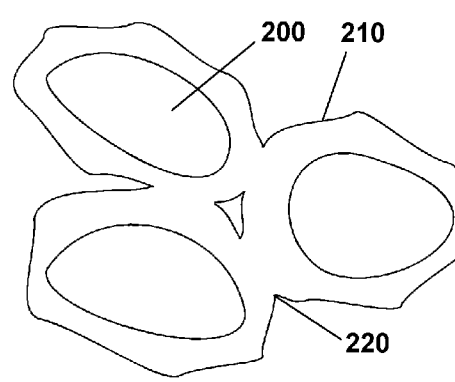
FIG. 2
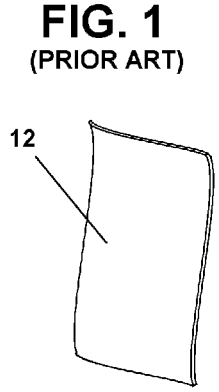
FIG. 3
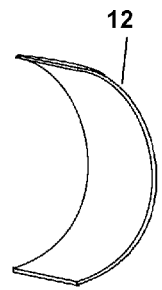
FIG. 3a
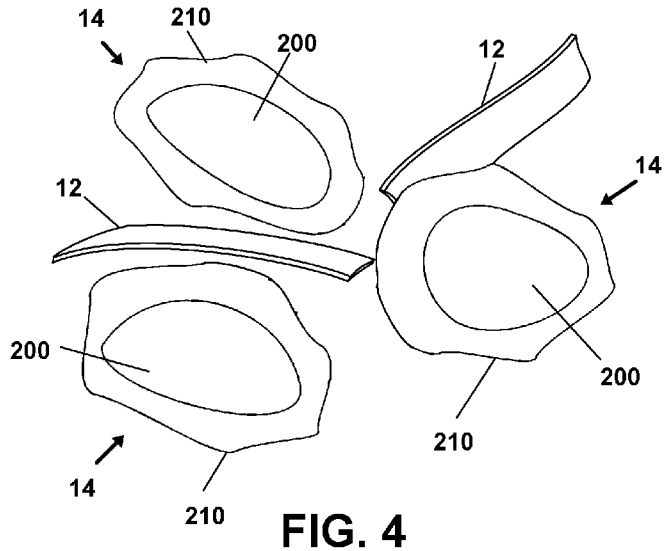
FIG. 4
FIG. 3b
FIG. 5
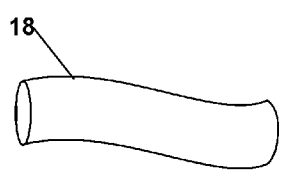
FIG. 6

THERMAL THERAPY DEVICE

BACKGROUND OF THE INVENTION

1. Field of the Invention

The present invention relates to thermal therapy devices. More particularly the invention relates to thermal therapy devices comprising a plurality of hydrated hydrophillic absorbers and a means for preventing clumping of the absorbers over extended cycles of freezing/melting.

2. Prior Art

Thermal therapy is a conventional method of rehabilitating injuries such as bruises and sprains to bone, muscle, ligaments, tendons, and skin. Heat therapy is often employed to loosen joint tissue while cold therapy is preferred for reducing swelling, pain, and to promote healing. Cold therapy is also known to be beneficial after surgery additionally for reducing swelling and promoting healing. By lowering the temperature of the injured tissue, the metabolic rate is reduced which allows the tissue to survive and recover during the period following the injury.

A conventional cold therapy method is simply to apply ice to the affected area. This can include wrapping bags of ice around the injury, however is not preferred due to the lack of temperature control and possible damage (frost-bite) to the skin and surrounding tissue. As a result, cold therapy can be applied with the provision of a re-freezable device which does exceed the cooling temperature and time recommended by medical professionals.

Prior art has made many attempts to provide thermal therapy devices which can be employed for many freezing/melting cycles and therefore provide extend use by the user. U.S. Pat. No. 5,800,491 to Kolen et. al., herein incorporated in its entirety by reference, teaches a thermal therapy device employing a mixture of discrete hydrophilic absorbers and a hydrating liquid mixture comprising a substantial amount of water which freezes under normal freezer conditions (32° F. to −20° F.) and increases the heat capacity of the therapy device.

In use, when freezing the device to Kolen, the water retained within the hydrophilic absorbers migrates out and freezes in discrete white ice crystals and, when thawed, melted water is reabsorbed by the hydrophilic absorbers. The water conventionally solidifies around the absorbers of which it migrates out, individual hydrophillic absorbers remain in discrete form due to the control of the water flow in and out of the hydrophilic absorbers. The device includes a flexible container with an air passage having an air permeable membrane which allows air to pass in and out of the container as the device expands/contracts during freezing/thawing cycles, respectively. There are also included a plurality of non-absorbing beads which are employed as a means for increasing the thermal resistance through the device. The provisions and features of the device allow the device to maintain substantial pliability in both the thawed and frozen states within a conventional operating period of 2 to 40 cycles. Pliability is desired since the device must conform to the curves and bends of the human body during application.

The device to Kolen is considered a great advance in the art, however, experimentation has shown that the device fails to maintain its pliable and flexible characteristics after extended cycles of freezing/thawing past the conventional operating period. This makes the device less desirable to users after prolonged operative employment. This is most commonly attributed to the process of 'clumping' of the discrete absorbers, when ice crystals forming on at least two adjacent absorbers bond or adhere together over prolonged and repeated freezing/thawing cycles which rigidizes the flexible container containing the absorbers. Despite the assertions in the disclosure to Kolen that the discrete absorbers retain their discrete forms over time, clumping has been shown to occur during the freezing cycle after prolonged and repeated use of the device; as the water migrates out and solidifies around the discrete absorbers, adjacent discrete ice/absorber formations will tend to bond together, creating clumps. In addition, the absorbers will gradually break down into ever small pieces with each usage, this also increases the tendency to clump.

Those skilled in the art could easily ascertain that repeated cycles of freezing/melting will cause the absorber material to degrade and wear. Therefor the ability to control water flow out of the hydrophilic absorbers during the freezing process is substantially diminished. As such, the once discrete formations will bond together and become large formations (clumps) which are rigid and not easily broken apart therefor inhibiting the pliable characteristic of the device. At this point the user will often discard the device and opt for other means for cold therapy.

Still further, an additional downfall noted about the device is the manner in which the device is frozen and/or stored by the user. The device to Kolen is intended to be placed within a users freezer, wherein as noted above the water migrates out of the discrete absorbers then solidifies in a discrete formation. During this process, the solidification of the liquid water into ice will increase the volume of the flexible container of which the absorbers and fluid mixture are contained within. The air membrane allows excess air escape the container in order to prevent a rupture of the container, however, there is still a substantial increase in the overall volume of the device. The device must be able to expand without resistance to insure that the ice forms in discrete formations around the absorbers. In the event that the device cannot freely expand, such as in a crowded freezer, the discrete ice/absorber formations will again tend to bond together into rigid clumps.

As such, there is a continuing unmet need for a thermal therapy device having hydrophillic absorbers and having means for preventing clumping of the discrete absorbers during freezing cycles. Such means for preventing clumping should preferably be providing by an added particulate which provides a physical separation means between at least two adjacent absorbers during the freezing cycle. Such a thermal therapy device can then be employed over extended cycles of freezing/melting without the occurrence of adjacent ice/absorber formations bonding (clumping) together. Such a device should provide a means for physical separation which is added to a mixture of hydrophillic absorbers and liquid mixture, which acts as a barrier to prevent discrete ice/absorber formations from clumping together.

Further, such a device should be provided to the user in a kit additionally comprising a rigid storage container component which can house the device during the freezing process and therefor allow the device to uninterruptedly expand to a predetermined volume. Such a container component can also include a means for visually ascertaining that the freezing cycle of the device is completed.

The forgoing examples of related art and limitation related therewith are intended to be illustrative and not exclusive, and they do not imply any limitations on the invention described and claimed herein. Various limitations of the related art will become apparent to those skilled in the art upon a reading and understanding of the specification below and the accompanying drawings.

SUMMARY OF THE INVENTION

The device herein disclosed and described provides a solution to the shortcomings in prior art and achieves the above noted goals through the provision of thermal therapy device comprising a plurality of hydrophillic absorbers, a hydrating liquid solution, and means for preventing clumping of adjacnet hydrophillic absorbers during the liquid-to-solid phase transition of the hydrophillic absorbers and liquid mixture under normal freezer conditions (32° F. to −20° F.).

The hydrophillic absorbers of the present invention can be of any suitable material known in the art. For example, the hydrophillic absorbers can be those outlined in the incorporated patent to Kolen et. al. Briefly, the hydrophillic absorbers can be formed from discrete acrylic polymer granules having a dehydrated size ranging from about 1 mm to about 6 mm. A preferred material is cross-linked polyacrylamide copolymer however can be formed of any material suitable for the purposes set forth in this disclosure.

The hydrating liquid mixture is preferably a solution of water and a humectant. The humectant can include one or a combination of propylene glycol, ethylene glycol, glycerin, dimethyl sulfoxide, and dimethyl fonnamide. However other suitable materials recognized by those skilled in the art may be employed, and are anticipated.

In accordance with a first preferred mode, the means for preventing clumping of adjacent discrete ice/absorber formations is provided by the addition of a plurality of physical barrier particulate added into the mixture of the hydrophillic absorbers and liquid solution. The physical barriers are preferably particulate of polypropylene, however can be any suitable saturated hydrocarbon or synthetic polymer suitable for the intended purpose. The particulate are preferably substantially planar, and may have flat, curved, curvilinear, or other non-flat profiles. The polypropylene or other barrier components are preferably mixed in a ratio of about 1-85% of the total anticipated volume of the mixture. The planar components can be sheets of polypropylene added to the mixture of hydrophilic absorbers and liquid solution which experimentation has shown to tend to position themselves between adjacent discrete ice/absorber formations during liquid-to-solid phase transition and therefore act as a means for physically separating at least two adjacent absorbers therefore providing a means for preventing clumping. As a result, the occurrence of adjacent formations bonding/clumping together during the liquid-to-solid phase transition is substantially reduced. Experimentation has shown that the operable life of the thermal therapy device is extended to at least 4 times longer than that of prior art devices. As such the device of the present invention is highly more marketable to users who often employ thermal therapy devices, such as athletes, medical professionals, and others.

In addition to reducing clumping, the plurality of planar components act to increase the thermal resistance through the thermal therapy device. Further, in other modes of the invention, the device may additionally include a plurality of hydrophobic beads which also increase the thermal resistance through the device. The beads may be in the form of spherical beads and/or other elongated shapes.

In accordance with at least one preferred mode, the mixture comprising one or any suitable combination of components from a group including the hydrophillic absorbers, hydrating liquid mixture, means for physical separation of adjacent absorbers, and hydrophobic beads are held within a flexible container that includes one or a plurality of air passages optionally covered with an air permeable membrane. The membrane can be formed from any material suitable for the intended purpose, for example poly-tetra-fluoro-ethylene (PTFE) treated with an oleophobic substance. By allowing air to pass in and out of the container as the water in the hydrating mixture transitions from liquid to solid, and visa versa, the pliability of the container is maintained throughout all phase cycles.

In still yet another mode, the device includes a storage container component which can be employed to store and protect the device when placed in a freezing environment, such as in a freezer. The storage container component provides a rigid housing for protecting the device from external forces which may cause the ice crystals forming on the exterior surface of the absorbers to bond together during the liquid-to-solid phase transition which further compromises the pliability of the thermal therapy device. The storage container includes at least one openable aperture allowing the user to place the device within an internal cavity of the container and retrieve it when needed. However, additional plurality of vent apertures may be provided to allow freezing climate to circulate within the cavity to aid in bringing the device to the freezing temperature. Still further, the storage container may include a means for visually ascertaining that the device has achieved a final frozen volume, and therefore the as used state.

With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Features, advantages, and objects of the invention will be brought out in the following part of the specification, wherein detailed description is for the purpose of fully disclosing the invention without placing limitations thereon.

BRIEF DESCRIPTION OF DRAWING FIGURES

The accompanying drawings, which are incorporated herein and form a part of the specification, illustrate some, but not the only or exclusive, examples of embodiments and/or features. It is intended that the embodiments and figures disclosed herein are to be considered illustrative rather than limiting. In the drawings:

FIG. 1 shows a side view of a prior art thermal therapy device comprising a mixture of hydrophillic absorbers and hydrating liquid solution.

FIG. 2 shows a view of the process of clumping of hydrophillic absorbers during the liquid to solid phase transition associated with prior art thermal therapy devices.

FIG. 3 shows a view of a particularly preferred mode of the planar barrier component.

FIG. 3a shows a view of another preferred mode of the barrier component having a substantially curved profile.

FIG. 3b shows yet another preferred mode of the barrier component having a substantially curvilinear profile.

FIG. 4 shows a representation of the as used mode of a plurality of planar barrier components added into a mixture comprising hydrophillic absorbers and hydrating liquid mixture.

FIG. 5 shows a view of a particularly preferred spherical hydrophobic bead component which can optionally be employed in the mixture.

FIG. 6 shows a view of another particularly preferred hydrophobic member formed as an elongated cylinder which can optionally be employed in the mixture.

DETAILED DESCRIPTION OF THE PREFERRED EMBODIMENTS OF THE INVENTION

Figure 7:
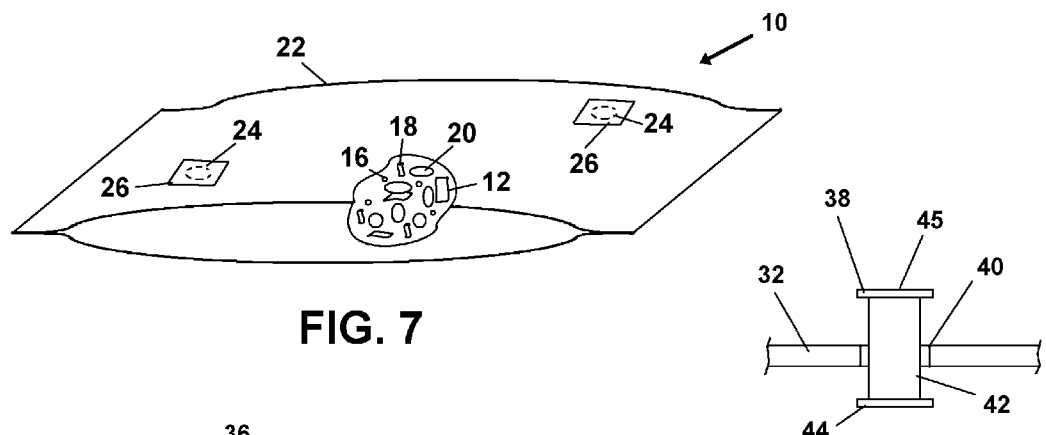
FIG. 7 depicts a particularly preferred mode of the device, with partial cut-away, showing a mixture comprising one or a combination of hydrophillic absorbers, planar barrier components, and hydrophobic components, enclosed within a flexible container having one or a plurality of air passages with air permeable membranes.
Figure 9:
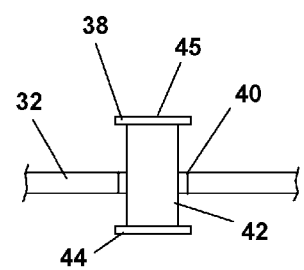
FIG. 9 shows a cross sectional view of the indicator viewed along line AA of FIG. 8.

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation.

Now referring to drawings in FIGS. 1-10, wherein similar components are identified by like reference numerals, there is seen in FIG. 1 a view of the prior art thermal therapy device 100. The prior art device 100 generally comprises a flexible container housing a plurality pre-hydrated hydrophillic absorbers 110. The device 100 is considered a great advance in the art as it provides a substantially pliable thermal therapy device 100 through a limited operative period of freezing/thawing cycles. However, experimentation has shown that the device 100 loses substantial pliability after prolonged and extended employment, and therefore fails to provide a most desirable thermal therapy device.

As depicted in FIG. 2, after prolonged employment of being subjected to conventional freezer temperatures and through conventional wear and tear by the user, water migrating out of the initially hydrated hydrophillic absorbers 200 freezes on the external surface of the absorber 200 forming ice crystals 210 wherein adjacent two or more formations bond 220 together creating clumps of a plurality of adjacnet absorber/ice formation. As such, the once discrete absorbers 200 are now packed in clumps within the flexible container of the prior art device 100, and pliability is substantially reduced. This creates a thermal therapy device which is undesirable to the user.

As such, in accordance with a first preferred mode of the present invention, an improved thermal therapy device 10 (FIG. 7) is provided by employing a mixture comprising one or a combination of components from a group of components including a plurality of hydrophillic absorbers, hydrating liquid mixture, means for physically separating two or more adjacent absorbers providing a means for preventing clumping, and hydrophobic insulating components providing means for defining a bulk thermal resistance of the device 10.

The hydrophillic absorbers are preferably formed from discrete acrylic polymer granules having a dehydrated size ranging from about 1 mm to about 6 mm. A preferred material is cross-linked polyacrylamide copolymer however the absorbers can be formed of any material suitable for the purposes set forth in this disclosure.

The hydrating liquid mixture is preferably a solution of water and a humectant. The humectant can include one or a combination of propylene glycol, ethylene glycol, glycerin, dimethyl sulfoxide, and dimethyl fonnamide. Still, other materials recognized by those skilled in the art which suitable for the intended purpose may be employed, and are anticipated.

FIG. 3 shows a view of a particularly preferred barrier particulate 12 as a means for physically separating the absorbers 200 and therefore providing a means for preventing clumping. The barrier 12 is preferably substantially planar, having a surface area in the range of 0.2 to 1.5 square inches. However, it is noted that the surface area of the barrier particulate 12 can be of values outside this range which are suitable for the intended purpose of physically separating adjacent absorbers and preventing clumping, and are anticipated. However, it is further noted and anticipated those skilled in the art may recognize other suitable non-planar shapes and forms of the barrier particulate which could provide a means for physically separating the absorbers 200 and therefore providing a means for preventing clumping, and therefore should not be considered limit to the preferred modes only.

The barrier particulate 12 herein can be formed of conventional materials such a synthetic polymer, Teflon®, however can be formed of any material suitable for the purposes set forth in this disclosure. For example the barrier 12 may be formed from portions of Teflon®, glass, polypropylene, or a suitable saturated hydrocarbon or synthetic polymer. Additionally, the barrier 12 can be flat planar as shown in FIG. 3, or alternatively the barrier 12 may have non-flat cross sectional profiles, such as a substantially curved profile (FIG. 3a) or a substantially curvilinear profile (FIG. 3b).

FIG. 4 shows a view of the operative employment of the barrier components 12 employed in a mixture of hydrophilic absorbers and hydrating liquid mixture. As can be seen, water migrating out of the initially hydrated hydrophillic absorbers 200 freezes on the external surface of the absorber 200 forming ice crystals 210. Clumping is generally defined when ice crystals 210 of at least two adjacent absorbers 200 bond or adhere together. However, the barrier components 12 will tend to migrate within the mixture to a configuration between adjacent hydrophillic absorbers 200 and prevent bonding 220 of adjacent ice crystals 210, therefore providing a means for preventing clumping. As such, providing utility as well as an advantage over prior art, discrete formations 14 of the absorbers 200 and crystals 210 are maintained over extended period of use and cycles of freezing/thawing, further allowing the device 10 to maintain pliability after such prolonged and extended periods of freezing/thawing cycles.

FIG. 5 and FIG. 6 show views of particularly preferred modes of the hydrophobic insulating components which can be optionally included into the mixture of hydrophillic absorbers, hydrating liquid mixture, and barrier particulate. In FIG. 5, a substantially spherical hydrophobic bead 16 is shown and can be introduced at 1-60% by volume into the mixture noted above. The bead 16 can be formed from insulating materials such as plastic, styrofoam or other suitable material. FIG. 6 shows another preferred mode of the hydrophobic component being a substantially elongated cylindrical member 18, also formed from insulating materials such as plastic, styrofoam or other suitable material. The hydrophobic components provide a means for increasing the thermal resistance through the device 10 such that the device 10 can be applied to therapy sites that cannot tolerate low temperatures. The elongated cylindrical member 18 may be preferred over the spherical bead 16 due to the higher surface area to volume ratio and therefore providing an enhanced means for increasing the thermal resistance.

It is noted and anticipated that although the various components forming the thermal therapy device 10 are shown in the most simple form, various components and aspects of the device may be differently shaped or slightly modified when forming the invention herein. As such those skilled in the art will appreciate the descriptions and depictions set forth in this disclosure or merely meant to portray examples of preferred modes within the overall scope and intent of the invention, and are not to be considered limiting in any manner.

FIG. 7 shows a view of a particularly preferred mode of the thermal therapy device 10. The device 10 is generally comprised of a flexible container 22 employed to contain a mixture comprising one or a combination of a plurality of pre-hydrated hydrophilic absorbers 20 (i.e hydrophillic absorbers and hydrating liquid mixture), means for physical separation between adjacent absorbers being barrier particulate 12, hydrophobic beads 16, and hydrophobic cylinders 18. The flexible container 22 is a water-impermeable container, such as one formed from synthetic resins. However there is additionally included one or a plurality of air passages 24 communicating through the sidewall of the container and optionally employing an air permeable membrane 26 covering the passage 24. The membrane 26 allows air to pass in and out of the container. The membrane 26 can be formed from any material suitable for the intended purpose, for example polytetra-fluoro-ethylene (PTFE) treated with an oleophobic substance.

Figure 8:
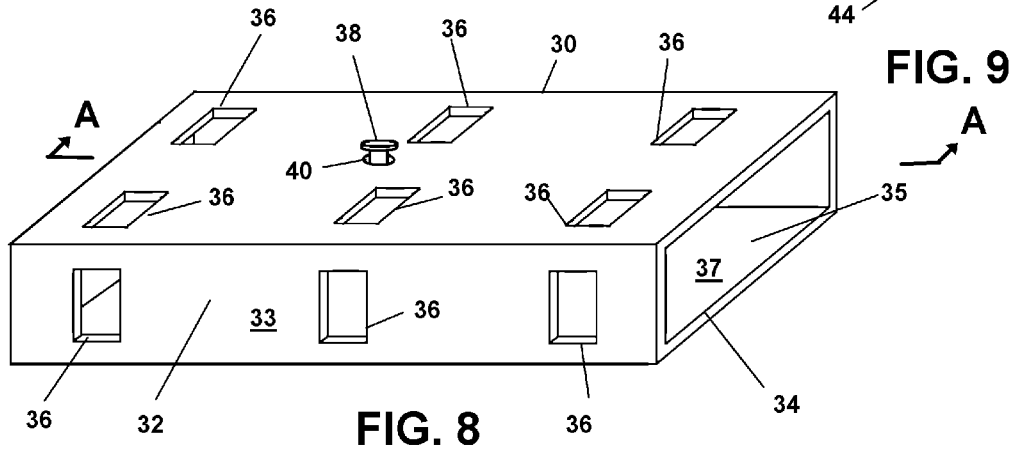
FIG. 8 shows a perspective view of a particularly preferred storage container component of the present invention, having a "pop-up" style indicator means.

FIG. 8 shows a view of a particularly preferred rigid openable storage container component 30 of the present invention which is especially well configured to store or house the device 10 when placed under freezing conditions, such as in a conventional freezer. The storage container is comprised of or a plurality of sidewalls 32 having exterior surfaces 33 and interior surfaces 37. The interior surfaces 37 of the sidewalls 32 further define an interior cavity 35. The container 30 preferably includes at least one open end 34. However in other modes the container 30 can be openable such that one or a plurality of sidewalls can be opened to provide access to the interior cavity 35. The open end 34 and cavity 35 are preferably configured to receive the device 10 in a stored mode. The cavity 35 is further preferably sized with an interior dimension which may correspond to a final expanded volume of the device 10 after freezing. As such, the device 10 can be communicated into the cavity 35 in a stored mode when the mixture is in the melted or thawed phase, and can freely expand to the final volume of the frozen phase of the mixture.

As noted previously, as the liquid mixture absorbed in the hydrated absorbers 20 migrates out and transitions from liquid to solid, the ice crystals forming on the exterior surface of the absorbers 20 will tend to increase the overall volume of the mixture and therefore cause an expansion of the flexible container 22. If the device 10 is not allowed to freely expand during this process, adjacent absorbers 20 will tend to bond together if there is external pressure applied between adjacent absorbers 20. This can occur if the device 10 is placed in a user's freezer and other objects are placed on top of it and impart external forces on the device 10. As such the rigid container 30 solves this problem. The interior cavity 35 is preferably substantially equal to the final frozen volume of the device 10.

Additional utility of the container 30 is provided through a means for ascertaining when the device 10 has reached its final volume which provides an indication to the user that the device 10 has achieved the operative frozen phase. In accordance with at least one preferred mode, the means for ascertaining is provided by a sliding indicator component 38 communicating through an 20 aperture 40 disposed on at least one sidewall. Shown more clearly in the cross sectional view of FIG. 9, the indicator component is comprised of an elongated body portion 42 having proximal and distal lip portions 44, 45 respectively. The body portion 42 is preferably configured for a translational engagement within the aperture 40. The lip portions 44, 45 are preferably sized and configured larger than the aperture 40 such that the body 42 of the indicator 38 cannot become disengaged from its engagement with the aperture 40.

Figure 10:
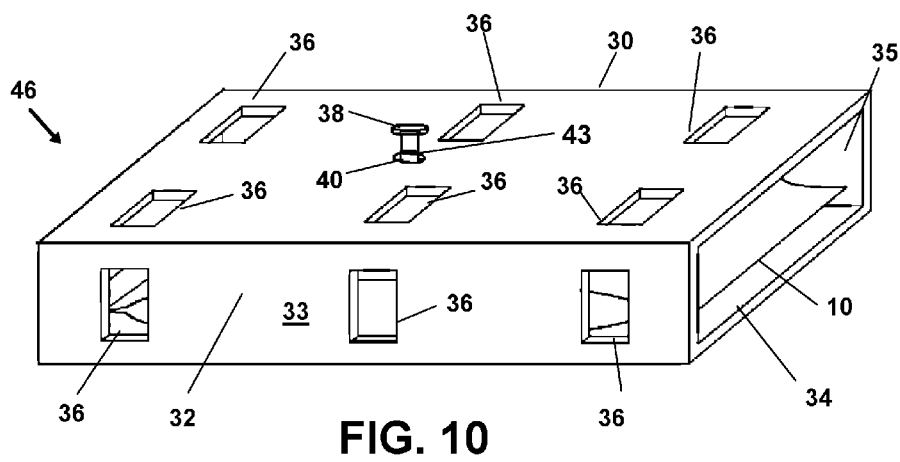
FIG. 10 shows a mode of the device which is providable to the user in a kit comprising the thermal therapy device and the storage container.

In use, and in a preferred mode, the indicator 38 and aperture 40 are disposed on a top sidewall of the container 30. As such, when the thawed mode of the device 10 is placed in the cavity 35, the indicator 38 will extend into the cavity 35 due to gravity. During the freezing of the device 10 within the cavity 35, the flexible container 22 of the device 10 will expand within the cavity 35 to the final volume and contact the indicator 38 as it expands, thereby translating a substantial portion of the indicator 38 out of the cavity 35 and above the top sidewall. The body 42 of the indicator 38 may include one or a plurality of indicia marking 43, for example viewable above the top sidewall as shown in FIG. 10. The user will know the device 10 has achieved the operative frozen state when the marking 43 is viewable by the user.

It is noted that upon reading this disclosure, those skilled in the art may recognize various other means for visually ascertaining the completed frozen phase of the device 10, which are considerably or slightly different than those disclosed, are considered within the scope and intent of the invention herein, and are anticipated within the scope of this patent.

Further, in FIG. 10, there is shown a particularly preferred mode of the invention wherein the device 10 is provideable to the user in a kit 46, comprising the thermal therapy device 10, and the storage container 30.

This invention has other applications, potentially, and one skilled in the art could discover these. The explication of the features of this invention does not limit the claims of this application; other applications developed by those skilled in the art will be included in this invention.

While all of the fundamental characteristics and features of the invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed:

1. A thermal therapy device comprising:
    a flexible, water-impermeable container conformable to the configuration of a therapy site of a user's body;
    a plurality of discrete, non-water-soluble, hydrophillic absorbers;
    a hydrating liquid mixture comprising water;
    a plurality of barrier particulates that prevent clumping of said hydrophillic absorbers when in a freezing environment,
        wherein individual ones of said plurality of barrier particulates are positioned between at least two adjacent individual ones of said plurality of hydrophilic absorbers during a liquid-to-solid phase transition of said water in said freezing environment; and,
    wherein the pliability of said container containing said plurality of hydrophilic absorbers, said liquid mixture, and said plurality of barrier particulates preventing clumping, is maintained over prolonged and extended cycles of freezing/thawing.

2. The thermal therapy device of claim 1 wherein said individual ones of said plurality of barrier particulates comprise a substantially planar material from a group of materials including plastic, polypropylene, saturated hydrocarbon, and polytetrafluoroethylene.

3. The thermal therapy device of claim 1 further comprising:
    a plurality of insulating members; and
    wherein said plurality of insulating members comprise one or a combination of shapes from a group of shapes including spheres and elongated cylinders.

4. The thermal therapy device of claim 2 further comprising:
    a plurality of insulating members; and
    wherein said plurality of insulating members comprise one or a combination of shapes from a group of shapes including spheres and elongated cylinders.

5. The thermal therapy device of claim 1 wherein said flexible, water-impermeable container comprises one or a plurality of air passages covered with an air permeable membrane allowing air to pass in and out of said flexible, water-impermeable container.

6. The thermal therapy device of claim 4 wherein said flexible, water-impermeable container comprises one or a plurality of air passages covered with an air permeable membrane allowing air to pass in and out of said flexible container.

7. The thermal therapy device of claim 2 wherein said individual ones of said plurality of barrier particulates comprise a cross sectional profile, said profile being one of flat, curved, or curvilinear.

8. The thermal therapy device of claim 6 wherein said individual ones of said plurality of barrier particulates comprise a cross sectional profile, said profile being one of flat, curved, or curvilinear.

9. The thermal therapy device of claim 1 wherein said plurality of barrier particulates comprise 1% to 85% by volume of the total volume of contents within said flexible, water-impermeable container.

10. The thermal therapy device of claim 7 wherein said plurality of barrier particulates comprise 1% to 85% by volume of the total volume of contents within said flexible container.

11. The thermal therapy device of claim 8 wherein said plurality of barrier particulates comprise 1% to 85% by volume of the total volume of contents within said flexible container.

12. A thermal therapy kit comprising:
    a flexible, water-impermeable container containing:
        a plurality of discrete, non-water-soluble hydrophillic hydrophilic absorbers,
        a hydrating liquid mixture comprising water,
        a plurality of barrier particulates that prevent clumping of said hydrophilic absorbers when in a freezing environment,
            wherein individual ones of said plurality of barrier particulates are positioned between at least two adjacent individual ones of said plurality of hydrophilic absorbers during a liquid-to-solid phase transition of said water in said freezing environment;
    a plurality of insulating members;
    an openable rigid storage container comprising of one or a plurality of sidewalls; and,
    an exterior surface, and an interior surface defining an interior cavity having a volume;
    said volume being substantially equal to an expanded as-used frozen volume of said flexible, water-impermeable container when in said freezing environment; and
    wherein said flexible, water-impermeable container is positionable into said interior cavity, and wherein said storage container comprises a rigid housing to protect said flexible, water-impermeable container when in said freezing environment.

13. The thermal therapy kit of claim 12 further comprising an indicator to visually ascertain when said flexible, water-impermeable container positioned in said interior cavity has reached said frozen volume.

14. The thermal therapy kit of claim 13 further comprising a plurality of vent apertures communicating from said exterior surface to said interior cavity.

* * * * *